(12) United States Patent
Melker et al.

(10) Patent No.: US 7,178,519 B2
(45) Date of Patent: Feb. 20, 2007

(54) INTUBATION TUBE PLACEMENT ASSESSMENT DEVICE

(75) Inventors: Richard Melker, Gainesville, FL (US); Dietrich Gravenstein, Gainesville, FL (US); Andrea Gabrielli, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 88 days.

(21) Appl. No.: 10/301,501

(22) Filed: Nov. 21, 2002

(65) Prior Publication Data

US 2004/0099263 A1   May 27, 2004

(51) Int. Cl.
*A61M 16/00* (2006.01)
(52) U.S. Cl. .............................. 128/200.26; 128/207.14
(58) Field of Classification Search .......... 128/200.26, 128/202.22, 202.27, 203.23, 203.12, 203.28, 128/204.18, 204.28, 205.13–205.17, 205.23, 128/207.14–207.17, DIG. 24, 205.12, 205.27; 604/100.01, 100; 600/538, 529, 532
See application file for complete search history.

(56) References Cited

U.S. PATENT DOCUMENTS

| | | | |
|---|---|---|---|
| 4,609,371 A | 9/1986 | Pizzino | |
| 4,728,499 A | 3/1988 | Fehder | |
| 4,879,999 A | 11/1989 | Leiman et al. | |
| 4,994,117 A * | 2/1991 | Fehder | 436/133 |
| 5,005,572 A * | 4/1991 | Raemer et al. | 128/207.14 |
| 5,179,002 A | 1/1993 | Fehder | |
| 5,279,289 A * | 1/1994 | Kirk | 128/205.23 |
| 5,360,003 A | 11/1994 | Capistrano | |
| 5,445,161 A * | 8/1995 | Huang | 600/532 |
| 5,487,731 A * | 1/1996 | Denton | 604/100.01 |
| 5,591,130 A * | 1/1997 | Denton | 604/100.02 |
| 5,749,358 A * | 5/1998 | Good et al. | 128/205.23 |
| 5,785,051 A * | 7/1998 | Lipscher et al. | 128/207.15 |

(Continued)

OTHER PUBLICATIONS

MacLeod, Bruce A., et al., "Verification of Endotracheal Tube Placement with Colorimetric End-Tital CO2 Detection." Annals of Emergency Medicine, 20:3 Mar. 1991, pp. 267-270 (78-81).*

Hayden, Stephen R., et al. "Colorimetric End-tidal CO2 Dectector for Verification of Endotracheal Tube Placement in Out-of-hospital Cardiac Arrest." Academic Emergency Medicine, 2 (6): 499-502 (1995).*

(Continued)

*Primary Examiner*—Justine R. Yu
*Assistant Examiner*—Amadeus Lopez
(74) *Attorney, Agent, or Firm*—Timothy H. Van Dyke; Beusse Wolter Sanks Mora & Maire

(57) ABSTRACT

A novel connection device, and method for its use, for connecting a volume displacement detection device and a gas composition detection device in line with an intubation tube is disclosed. The connection device allows a user to combine two systems commonly employed by medical personnel to assess the location of an intubation tube placed into a patient. The two systems have alternate means of assessing the location of an intubation tube in a patient and therefore, when combined into a single unit via the connection device, improve the accuracy of placing a tube in a desired location while reducing or eliminating complications associated with misplacement. A kit comprising components that may be assembled to provide a device for assessing the proper placement of an intubation tube in a patient is also disclosed. The kit may be used in any environment, but is particularly well suited for emergency, pre-hospital settings requiring intubation where quick assembly of the components is essential.

27 Claims, 5 Drawing Sheets

U.S. PATENT DOCUMENTS

| | | | | |
|---|---|---|---|---|
| 5,873,361 | A | * | 2/1999 | Hakala .................. 128/204.23 |
| 5,885,248 | A | * | 3/1999 | Denton .................. 604/100.03 |
| 6,149,603 | A | * | 11/2000 | Parker ......................... 600/532 |
| 6,202,646 | B1 | * | 3/2001 | Camodeca et al. ..... 128/207.14 |
| 6,584,974 | B1 | * | 7/2003 | Ratner .................. 128/205.23 |

OTHER PUBLICATIONS

Nunn, J.F. "The oesophageal detector device." *Anaesthesia* 1988;43:804.

Haridas, RP "Oesophageal Detector Devices." *Update in Anaesthesia* 1997;7:6(1).

O'Leary, J.J. et al. "A Method of Detecting Oesophageal Intubation or Confirming Tracheal Intubation." *Anaesthesia and Intensive Care* 1988; 16: 299-301.

Wee, M.Y.K. "The oesophageal detector device." *Anaesthesia* 1988 43;27-29.

Garnett, A. Randolph et al., "End-Tidal Carbon Dioxide Monitoring During Cardiopulmonary Resuscitation"*JAMA* 1987; 257: 512-515.

Ornato, Joseph P., et al. "Multicenter Study of a Portable, Hand-Size, Colorimetric End-Tidal Carbon Dioxide Detection Device." *Annals of Emergency Medicine* 1992; 21:518-523.

Pelico, Maria et al., "Out-of-hospital Experience with the Syringe Esophageal Detector Device." *Acad Emerg. Med* 1997: 4:563-568.

* cited by examiner

INTUBATION TUBE PLACEMENT ASSESSMENT DEVICE

FIELD OF THE INVENTION

The present invention is directed to a device used to connect two or more intubation placement detectors in line with an endotracheal tube (ETT) to provide rapid, alternative methods of assessing whether an ETT has been properly placed in the trachea of a patient.

BACKGROUND OF THE INVENTION

Ventilation of the lungs is essential to life. Patients in need of medical attention often require assistance with breathing as a result of injury, trauma, or airway obstruction. In an apneic patient, the lungs must be artificially ventilated to ensure proper oxygenation and exchange of gasses within the body. Endotracheal intubation is the technique of placing an endotracheal tube (ETT) into the trachea of a patient, for the purposes of establishing an airway. It is estimated that over 18 million intubations are preformed each year in the US, the majority in the operating room. Because of the close proximity of the esophagous to the trachea, an intubationist may accidentally place the ETT into an esophagous. If the error is detected immediately, no harm results. However, if the incorrect placement is not recognized and the ETT repositioned, within a few minutes irreversible brain damage and/or death may result, due to the lack of oxygen. In an ideal setting, an intubationist places an ETT in one hand and visualizes the glottic opening of the airway by introducing a larygoscope into the mouth. The ETT is then carefully passed into the trachea and attached to a source of oxygen. However, even under such controlled conditions inadvertant esophageal intubations have been reported. (White, S. J. and C. M. Slovis, *Acad Emerg Med* 1997:4:89–91) This problem is magnified in out-of-hospital intubations performed, or in the hospital outside of the OR and ER wards and intensive care units under less than ideal conditions such as, for example, at the scene of an accident, or within an ambulance in route to a hospital. Under such stressful and often chaotic conditions, misplacement of an ETT in a patient is not uncommon.

In an effort eliminate the danger inherent in unrecognized esophageal intubation, numerous clinical methods and devices have been developed to rapidly assess tube placement. Qualitative methods include direct visualization, observation of chest movement with bag inflation, auscultation of breathing sounds, absence of epigastric sound with ventilation, presence of exhaled tidal volume, reservoir bag compliance, endotracheal cuff maneuvers, absence of air escape, tube condensation with exhalation, absence of gastric contents within the tube and others (O'Connor, R. E. R. A. Swor *Prehospital Emergency Care* July–Sept. 1999). Each of these methods have utility in a limited range of clinical conditions.

Quantitative methods have also been employed to better assess endotracheal tube placement. The most common quantitative means to document correct placement of an endotracheal tube (ETT) is to sense carbon dioxide during the exhalation phase of ventilation. The success of this method is based on the difference between the $CO_2$ concentration in exhaled air (5%) and the $CO_2$ concentration in esophagael gas (0.2%–0.3%). Documentation of carbon dioxide in the exhaled breath has become the accepted standard for verifying the correct placement of an endotracheal tube, unless the location can be directly visualized, for instance, with a fiberoptic bronchoscope. Numerous devices have been developed for assessing proper endotracheal tube placement through detection of $CO_2$, the utility of each varying with the particular clinical condition.

The most common $CO_2$ detection device employed in hospitals is the capnometer. This device is used to monitor the concentration of exhaled carbon dioxide in order to assess the physiologic status of a patient. The device comprises an infrared sensor that continuously monitors and displays $CO_2$ concentration and generates a waveform (capnogram) that is correlated with a patient's respiratory cycle to quantitatively assess the adequacy of ventilation.

However, these devices are less reliable when there is a pulmonary embolis or a patient is in cardiac arrest. (Garnett, A R et al., *JAMA* 1987; 257: 512–515) Further, traditional capnometers are expensive, sophisticated, and fragile instruments requiring careful calibration and a source of power, making their use in out-of hospital procedures impractical. Thus, in emergency-type settings, a capnometer may be inadequate. In those situations, alternative devices are employed. The most reliable method for verifying proper tube placement in out-of hospital applications is through use of an end-tidal carbon dioxide detection device (Ornato, J P *Ann. Emerg Med* 1992; 21:518–523) The EasyCap End-Tidal $CO_2$ Detector (Nellcor-Mallincrodt-Tyco) is an inexpensive, disposable device that quickly attaches to an ETT to sense exhaled $CO_2$. With each breath, $CO_2$ exhaled passes over an indicator in the device that has been treated with a chemical that turns color in response to high $CO_2$ concentration. Thus, a change in color of the indicator is indicative of proper placement of the ETT in the trachea because of the substantially higher concentration of $CO_2$ in exhaled air as previously discussed. Tube placement anywhere but the trachea will not yield a color change. However, even if the ETT is properly placed, the EasyCap, like the more expensive capnometer, is inadequate in those instances where a patient lacks a pulse or has very poor pulmonary perfusion because without $CO_2$ exchange from pulmonary arterial blood to alveoli, insufficient CO2 will be exhaled to produce a color change.

To overcome these problems, other devices that do not directly depend on the detection of $CO_2$ have been developed. These esophageal detector devices (EDD), work on principles of gas volume displacement and depend on the structural difference between the trachea and the esophagus. In one embodiment, a catheter-tip syringe is connected to an ETT via a length of rubber tubing (Wee, M Y K *Anaesthesia* 1988 43:27–29) In use, negative pressure is created within the ETT through aspiration of the syringe chamber, i.e. withdrawal of the plunger from the syringe. If the ETT is placed in the esophagus, the walls of the esophagus collapse upon the ETT in response to this negative pressure, which in turn restricts air-flow that can be easily detected as resistance to plunger movement. However, when the ETT is placed in the trachea this negative pressure is incapable of causing the more rigid trachea to collapse, thereby allowing free exchange of air. Thus, free movement of the plunger is indicative of proper placement within the trachea. (O'Leary J. J. *Anaesthesia and Intensive Care* 1988; 16: 299–301) In an alternate embodiment, a rubber bulb is attached to an ETT. (Nunn, J F. *Anaesthesia* 1988;43:804) In use, the bulb is compressed prior to attachment to the ETT to create a negative pressure within the ETT. As described above, if the tube is placed within the esophagus air passage becomes restricted as the esophageal walls collapse around the ETT, but air freely flows if the ETT is properly placed in the trachea. Thus, passive re-inflation of the bulb is indicative of tracheal intubation, while the failure of the bulb to re-inflate is indicative of esophageal intubation. Each of these devices is portable, inexpensive, easily assembled and provides faster assessment of ETT position than both the capnometer and EasyCap described above, making them particularly well suited for intubations. performed outside the operating room (e.g. in the recovery room, emergency room, intensive care unit and out in the field). Further, these devices are useful in patients experiencing cardiac arrest because the test results do not depend upon the presence of $CO_2$ in exhaled gas (Haridas, R P *Update in Anaesthesia* 1997;7:6(1)) However, regurgitation of gastric air, distension of the esophagus with air, or an EDD that is not airtight may cause the bulb to re-inflate, giving a false impression of tracheal intubation when the tube is in fact in the esophagus. (Haridas, R P *Update in Anaesthesia* 1997; 7:6(3)) Further, although these devices are highly accurate when used in a hospital setting, studies indicate that they are only 50% accurate when used in the field by paramedics (Pelicio, M. *Acad Emerg. Med* 1997:4563–568)

The National Association of EMS Physicians has recognized that no single technique for assessing ETT tube placement currently used is completely reliable in all circumstances. (O'Connor, R. E. and R. A. Swor *Pre-Hospital Emergency Care*; July-Sept. 1999) Based on the inherent limitations in each device, it has become apparent to the authors that the optimal method of detecting proper ETT placement, particularly in out-of-hospital settings would incorporate both concepts of $CO_2$ detection and gas volume displacement to increase the accuracy of ETT placement to near 100%.

SUMMARY OF THE INVENTION

The present invention comprises a connection device useful in connecting a $CO_2$ detection device and a volume displacement device in line with an endotracheal tube (ETT). The device further comprises at least one positive pressure response valve and at least one negative pressure response valve to allow a user to control the movement of gas. By combining two or more existing ETT placement detectors in one unit, the present device allows a user to rapidly obtain alternate quantitative measurements of ETT placement in a patient in wide variety of clinical settings, both in and out of a hospital. The primary benefit of the present device is the ability to quickly discern with almost complete certainty the location of an ETT. Since incorrect placement of an ETT is not uncommon in situations of low blood flow, particularly cardiac arrest, this device offers several advantages over existing device, including improved specificity, sensitivity and full operation without the need for an electrical hookup. The benefit to the patient in any environment is obvious.

DESCRIPTION OF THE PREFERRED EMBODIMENT

Figure 1:
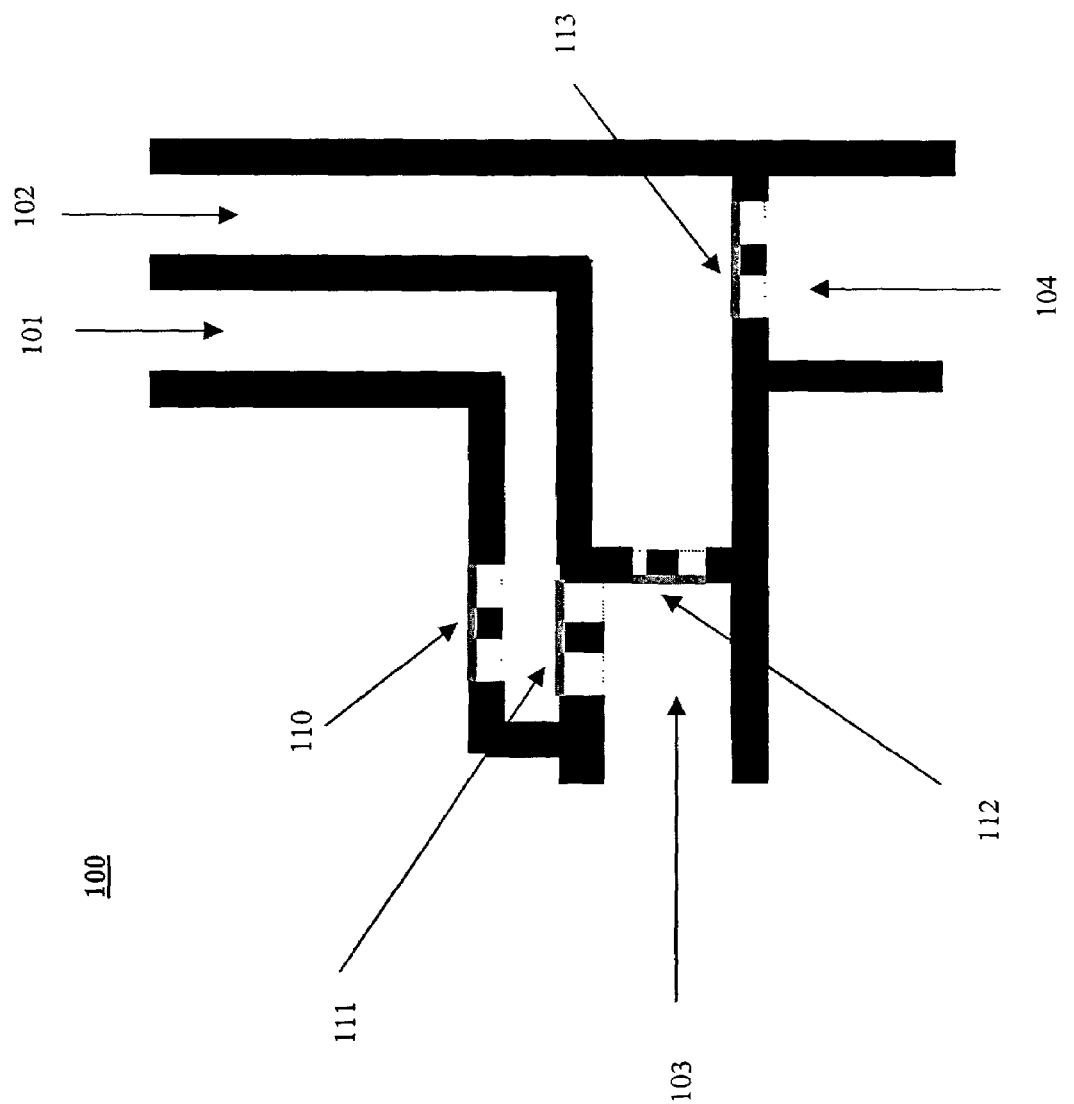
FIG. 1 Depicts one embodiment of a device used to connect multiple endotracheal tube placement detection devices in line with and endotracheal tube.

FIG. 1 shows a novel device, generally represented at 100, used to connect both a $CO_2$ detection device and a volume displacement detector in line with an ETT. In a preferred embodiment the device comprises first 101 and second 102 volume displacement detector portals, a $CO_2$ detector portal 103 and an endotracheal tube portal 104. The portals 101, 102, 103 and 104 are configured to connect with other appropriate devices via slip fittings, friction fittings, threaded fittings, or similar detachable fittings. The device comprises first 111 and second 113 positive pressure response valves which open when positive pressure is applied to the device 100 (see FIGS. 2B and 3B). First 110 and second 112 negative response valves are also incorporated into the device 100 and configured such that they open when negative pressure is applied to the device 100. (see FIGS. 3A and 3B) Preferably, the device is manufactured from inexpensive material such that it may be disposed of following use.

Figure 2A:
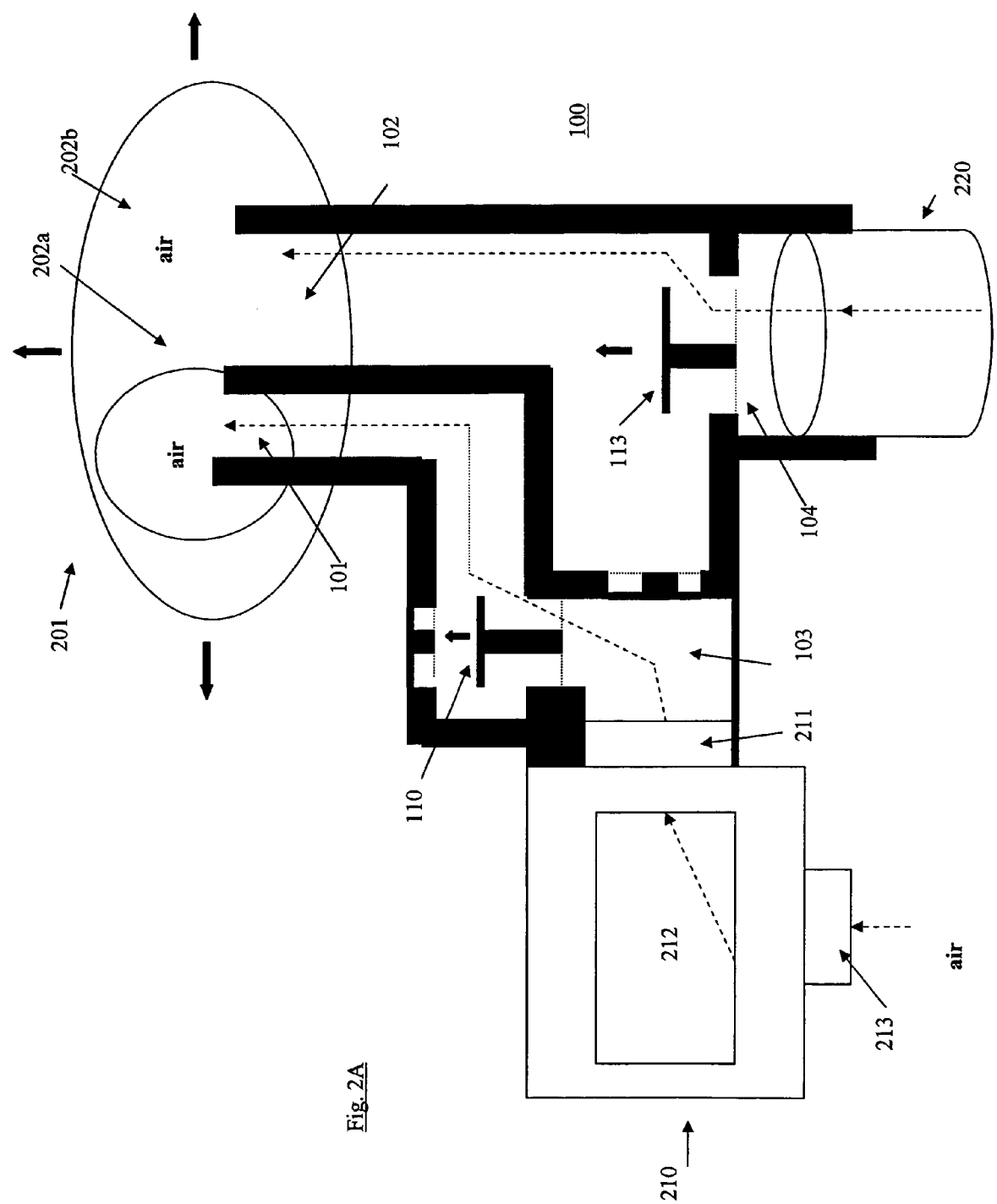
FIG. 2A Depicts one embodiment of the device with a bulb-in-a-bulb volume displacement device, a CO2 detection device and an endotracheal tube connected together as a system. As shown the volume displacement device has been employed to create a negative pressure in the system to retrieve a sample of gas.

FIG. 2A shows one embodiment of the device with an EASYCAP™ $CO_2$ detector, a bulb-in-a bulb volume displacement detector, and an endotracheal tube connected. The device 100 is connected to a volume displacement detector 201, which preferably comprises an inner balloon 202*a* enclosed within an outer balloon 202*b*. The volume displacement detector 201 is connected with the device 100 such that the detectors' inner balloon 202*a* communicates with the first volume displacement detector portal 101, and the detectors' outer balloon 202*b* communicates with the second volume displacement detector portal 102. A $CO_2$ detector 210 is connected to the device 100 via the $CO_2$ detector portal 103. As shown the $CO_2$ detector comprises an intake port 211 leading to a $CO_2$ indicator 212 which may be visualized by a user, and an exhaust port 213. An endotracheal tube (ETT) 220 is connected to the device 100 via the endotacheal tube portal 104. These components are assembled as a system having a system volume and a system pressure. In use, a three step process is commenced to obtain two indications of the proper placement of an ETT tube. First a clinician inserts the endotracheal tube into the mouth or nose and throat of a patient. Second, a negative pressure is created in the system. This is done by compressing the volume displacement detector 201 and then connecting it to the device 100. As the detector 201 attempts to regain its original shape and by increasing its volume, a partial vacuum (negative pressure) is created in the system. This negative pressure forces both first 110 and second 112 negative pressure response valves to open. As the first valve 110 opens, atmospheric air is drawn into the $CO_2$ detector 210 via an exhaust port 213, over an indicator 212, out of the detector 210 via the intake port 213, and into the device 100 where it passes through the open first valve 110 and into the inner balloon 202a to aid re-inflation. In this instance, the $CO_2$ detector does not exhibit a color change because there is insufficient $CO_2$ in atmospheric air to activate the indicator 212. Simultaneously, the second negative pressure response valve 113 opens. In response to the negative pressure generated, gas moves out a patient, passes through the ETT 220, through the open second negative pressure response valve 113 and into the outer balloon 202b. If the tube is misplaced into the esophagus, the negative pressure created within the ETT will cause the flexible walls of the esophagus to collapse around the end of the tube, thereby preventing air from flowing through the valve 113 and into the outer balloon 202b. If however, the tube is properly placed into the trachea, the rigid, ringed walls of the trachea will not collapse around the tube in response to the negative pressure, and air will freely flow from the patient through the valve and into the outer balloon 202b causing it to re-inflate. Rapid, passive inflation of the detector 201 is indicative of tracheal intubation. However, if the tube is mistakenly placed into the esophagus, the detector may passively inflate as a result of gastric distension or other causes as previously described, and provide a false reading. Thus, to ensure accurate assessment of ETT placement, a second measurement is employed.

Figure 2B:
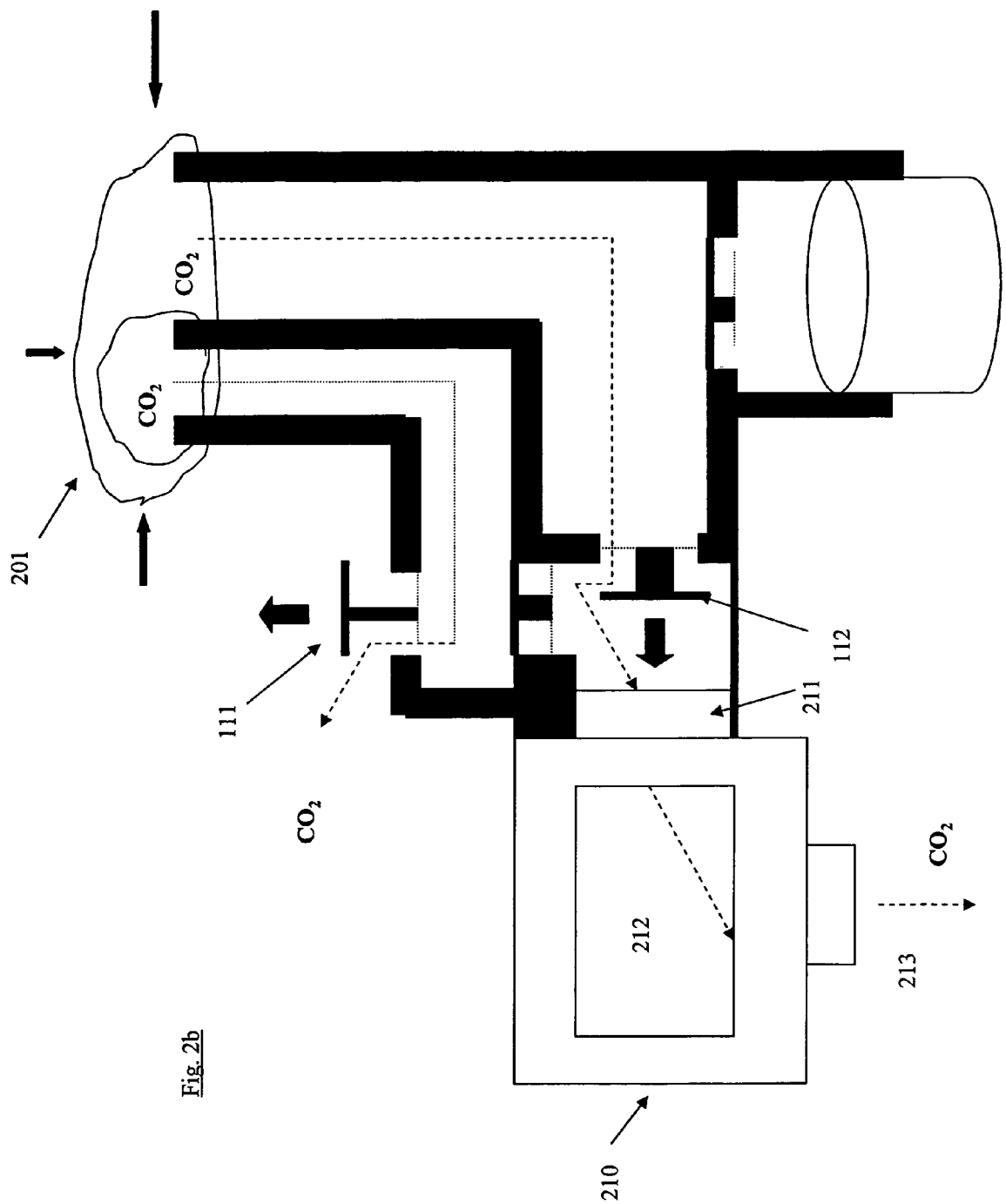
FIG. 2B Depicts one embodiment of the device with a bulb-in-a-bulb volume displacement device, a CO2 detection device and an endotracheal tube connected together as a system. As shown the volume displacement device has been employed to create a positive pressure in the system to force the gas collected into a $CO_2$ detector for analysis.

FIG. 2B depicts the third step of the process which comprises compressing the volume displacement detector 201 thereby decreasing the system volume and increasing the system pressure which forces gas retrieved from second step, out of the detector, through first 111 and second 112 positive pressure response valves, and into a $CO_2$ detection device 210. As shown, an EasyCap End Tidal $CO_2$ detector (Nellcor-Mallincrodt-Tyco) is employed as the $CO_2$ detector. However, one skilled in the art will recognize that multiple variations on $CO_2$ detection devices fall within the scope of this disclosure. When a user compresses the volume detector device 201, gas from the inner balloon 202a is forced into the device 100, causing the system volume to decrease and the system pressure to increase which in turn forces a first positive pressure response valve 111 to open, whereupon the gas escapes to the outside environment. Simultaneously, gas from the outer balloon 202b is forced into the device 100, which in turn forces a second positive pressure response valve 112 to open. This gas proceeds through the valve 112 and into the $CO_2$ detector 210 via the intake port 211. The gas then passes over a $CO_2$ indicator 212 before exiting the detector 210 via an exhaust port 213. If the ETT is properly placed in the trachea, this gas will have a $CO_2$ concentration sufficient to trigger a color change in the detector that is indicative of tracheal intubation. If the ETT has not been properly placed, the gas will have a low $CO_2$ concentration indicating it has come from the stomach or area other than the trachea, and no color change will occur.

Figure 3A:
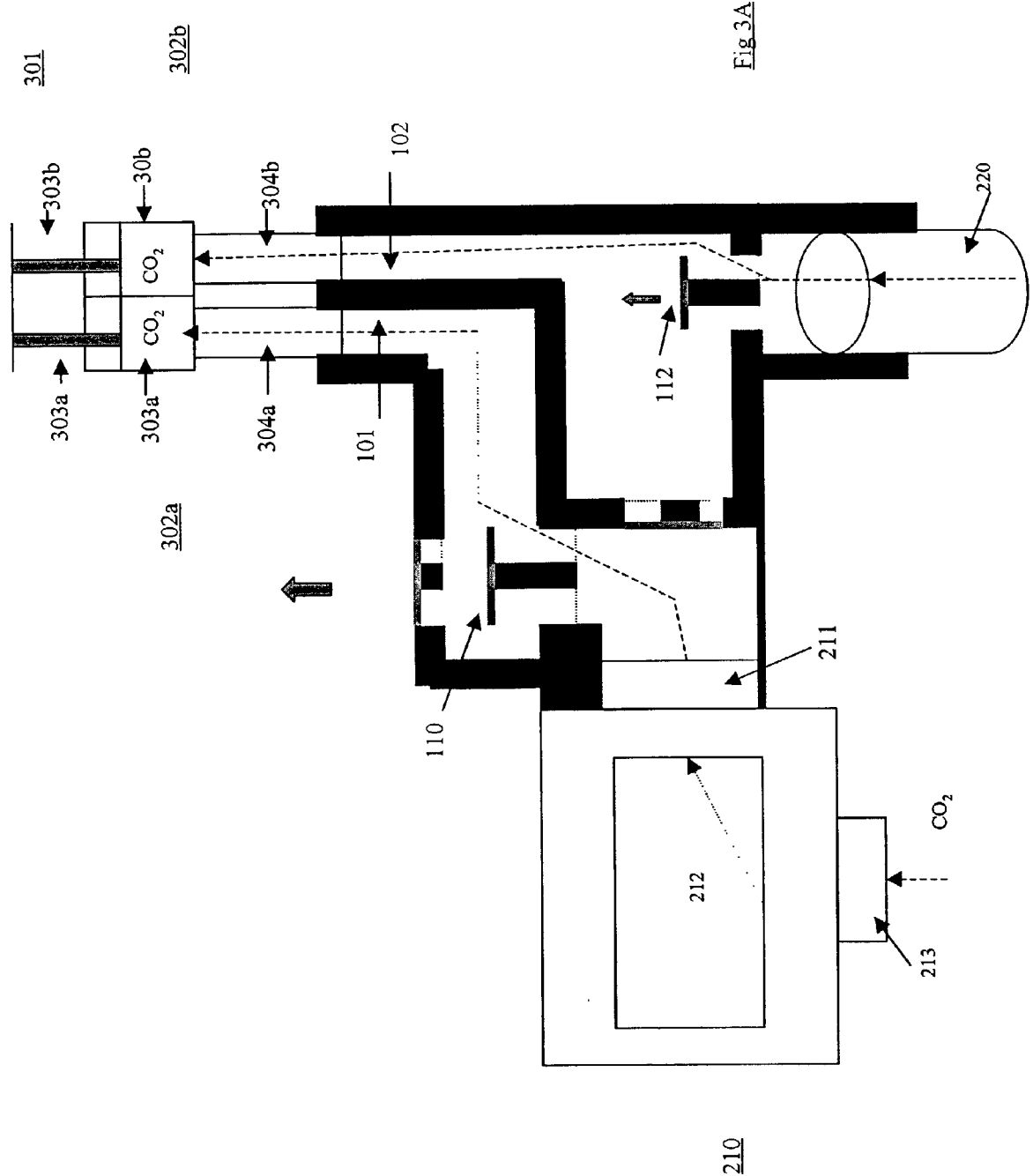
FIG. 3A Depicts one embodiment of the device with a dual syringe volume displacement device, a CO2 detection device and an endotracheal tube connected together as a system. As shown the volume displacement device has been employed to create a negative pressure in the system to retrieve a sample of gas.

In another embodiment, dual syringes are substituted for the bulb-in-a-bulb design shown in FIGS. 2A and 2B. All other elements remain the same. FIG. 3A shows the device with a preferred embodiment of a dual syringe 301 design attached. The dual syringe comprises first 302a catheter-tip syringe having a plunger 303a and a barrel 304a, and second 302b catheter-tip syringe having a plunger 303b and a barrel 304b. The first syringe 302a and second syringe 302b are connected to first 310a and second 310b lengths of tubing which are in turn connected to a first 101 and second 102 volume displacement device connectors respectively. Preferably, the dual syringes are connected together such that first 303a and second 303b plungers operate in tandem, and first 304a and second 304b barrels can accumulate a volume of gas from different locations, i.e. atmosphere, or patient. When all components are connected together, a system having a system volume and a system pressure is created.

Figure 3B:
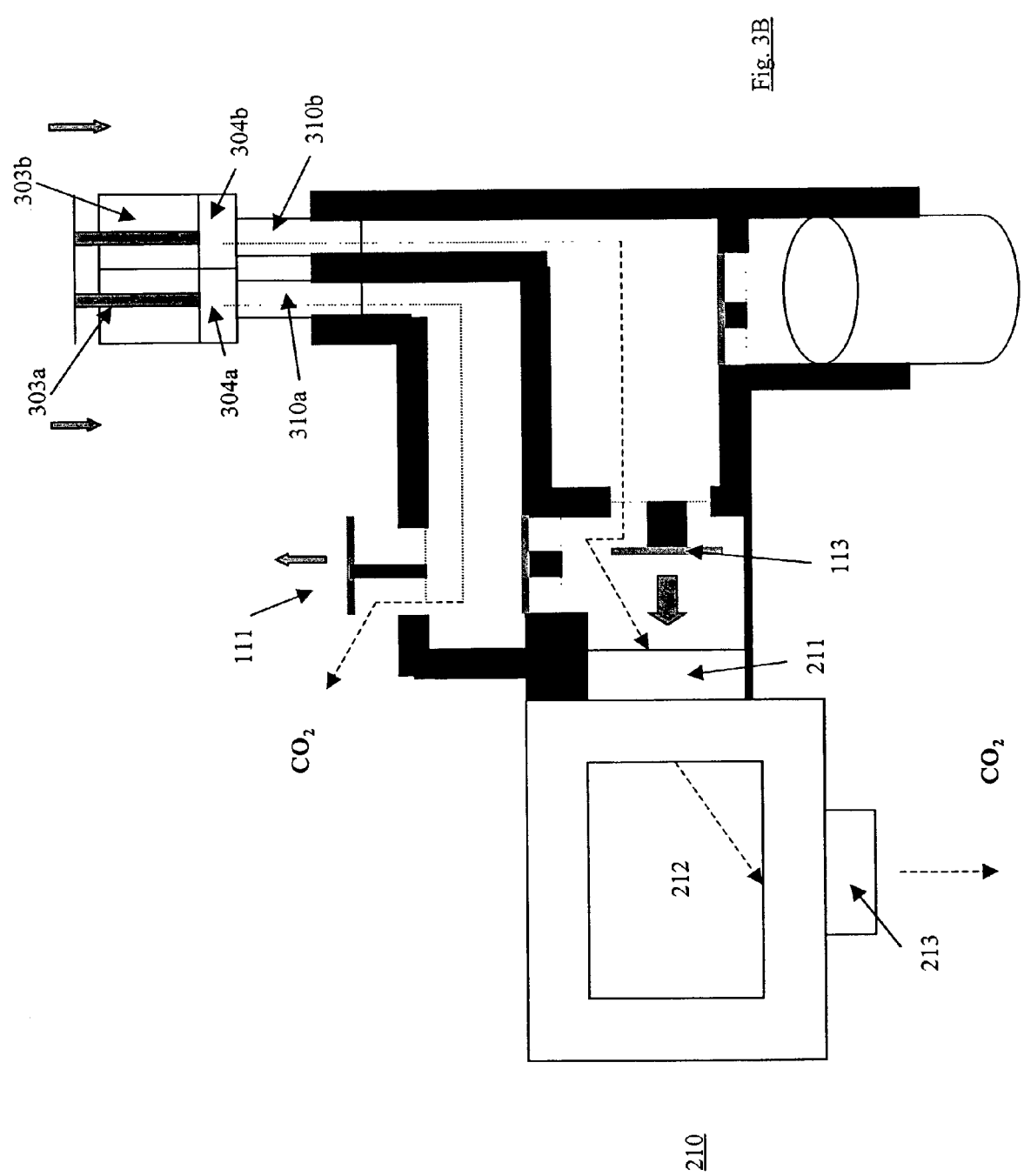
FIG. 3B Depicts one embodiment of the device with a dual syringe volume displacement device, a CO2 detection device and an endotracheal tube connected together as a system. As shown, the volume displacement device has been employed to create a positive pressure in the system to force the gas collected into a $CO_2$ detector for analysis.

Like the system described in FIGS. 2A and 2B, use of this embodiment requires three steps. First, a clinician inserts an endotracheal tube into the mouth or nose and throat of a patient. FIG. 3A depicts the second step of the process. Prior to connecting the first 310a and second 310b lengths of tubing to the first 101 and second 102 volume detection device connectors, the syringe plungers pushed toward the tips of the dual syringe. A negative pressure is then created in the system by simultaneously withdrawing the plungers from the syringe barrels. A partial vacuum (negative pressure) is created which forces the first 110 and second 112 negative pressure response valves to open. Atmospheric air is drawn through the $CO_2$ detector, through the first valve 110 and into the first barrel 304a in a manner identical to that described for the inner balloon 202a (see FIG. 2A). Simultaneously, air is drawn through the ETT 220, through the open second valve 112 and into the second barrel 304b. If the ETT is accidentally placed in the esophagus, the walls will collapse around the end of the ETT, making withdrawal of the first 303a and second 303b plungers difficult. Thus, recoil of the plungers following withdrawal is evidence of improper intubation, whereas free movement of the plungers is evidence of proper intubation. FIG. 3B depicts step three of the process which comprises creating a positive pressure in the system to force gas collected from step two out of the first 304a and second 304b barrels of the dual syringe 301 and into a $CO_2$ detection device 210. First 303a and second 303b plungers are pushed toward the tips of the dual syringe thereby decreasing the system volume and increasing the system pressure to force the gas through out of the barrels. Gas is forced out of the first 304a barrel, passes through the first 310a length of tubing, and into the device 100 which forces open the first positive pressure response valve 111 to allow the gas to escape to the environment. Simultaneously gas is forced out of the second barrel 304b, through the second 310b length of tubing and into the device 100 which forces a second 113 positive pressure response valve to open, allowing gas to move into the detector 210. Gas enters the detector 210 via the intake port 211, passes over the indicator and then out of the device 210 via the exhaust port 213. If the tube is properly situated in the trachea, the gas will contain a concentration of $CO_2$ sufficient to trigger the indicator.

Each detector provides a different mode. i.e. calorimetric, visual, etc., of assessing the placement of an ETT. The device allows for the assemblage of a wide variety of detection devices to cover all environments in which it may be employed. The device, may be used anywhere to assess ETT placement, but is primarily designed for use outside a fully equipped hospital operating room, such as, for example, in an ambulance or other pre-hospital setting. Through combining two efficient ETT placement detection devices, in one system, this invention increases the accuracy of endotracheal tube placement to almost 100%. Use of this device to create an assemblage of detection devices significantly decreases the risk of improper tube placement not uncommon in emergency-type settings, or where a patient has low or no cardiac output. The, device is inexpensive, reliable, simple to use, capable of being incorporated with an ETT quickly and effectively by any user regardless of the level of training, does not require a power supply, and is not subject to calibration errors. Because the present device allows assemblage of a system that can assess ETT placement with practical certainty under any set of conditions, the present device is needed in the field to provide the best, safest level of healthcare possible.

One knowledgeable in the art will immediately recognize that the present invention is not limited to using a dual syringe, or bulb-in a bulb volume displacement device. Any device capable of creating a negative pressure which is adaptable for use with the present device falls within the scope of this disclosure. Similarly, the invention is not limited to use of an EasyCap or capnometer $CO_2$ detection, nor is it limited to CO2 detection devices in general. Any gas detection device that can be adapted for use with the present device that aids in assessing the location of an ETT falls within the scope of this disclosure. Also, other devices utilizing audible, visual, tactile and electrical signals to indicate the position of an ETT may also be employed.

What is claimed is:

1. A connection device for use in assessing placement of an intubation tube in a patient comprising a tubular housing comprising
    a first portal adapted for connecting to a volume displacement detector, said first portal comprising first and second openings defined therein;
    a second portal adapted for connecting to a gas composition detector;
    a third portal adapted for connecting to an intubation tube;
    an exhaust outlet;
    a first conduit defined in said housing and configured such that (i) gas from said third portal may flow to said first opening of said first portal upon application of negative pressure at said first portal and (ii) gas from said first opening of said first portal may flow to said second portal upon application of positive pressure at said first portal; and
    a second conduit defined in said housing and configured such that (i) gas from said second portal may flow to said second opening of said first portal upon application of negative pressure at said first portal and (ii) gas from said second channel of said first portal flows to said exhaust outlet upon application of positive pressure at said first portal.

2. The connection device of claim 1, wherein said first and second conduits comprise at least one positive pressure response valve and at least one negative pressure response valve disposed along said first and second conduits, wherein said at least one positive pressure response valve and said at least one negative pressure response valve open in response to positive or negative pressure, respectively, applied in said first and second conduits to permit bi-directional flow of gas into and out of said housing.

3. The connection device of claim 2, wherein said device is adapted for quick assembly with a volume displacement detector, a gas composition detector and an intubation tube.

4. The connection device of claim 3, wherein said connection device, said volume displacement detector, said gas composition detector and said intubation tube create a system for assessing proper intubation tube placement in a patient.

5. The connection device of claim 4, wherein following intubation of a patient, gas can be withdrawn from a patient into said connection device to selectively communicate with said volume displacement detector or said gas composition detector.

6. The connection device of claim 5, wherein said system provides rapid, alternative measurements to assess intubation tube placement in a patient.

7. The connection device of claim 6, wherein said measurements are quantitative, qualitative or both.

8. The connection device of claim 7, wherein said device is constructed of inexpensive materials such that said device may be discarded after use.

9. The connection device of claim 8, wherein said intubation tube is an endotracheal intubation tube.

10. The connection device of claim 1, wherein said volume displacement detector comprises a bulb having at least one collapsible, self-inflating cavity, said bulb configured for connection to said connection device.

11. The connection device of claim 10, wherein said bulb is visibly responsive to pressure differentials within different passages of a patient coincident with the expiratory and inspiratory phases of a respiratory cycle.

12. The connection device of claim 10, wherein said device is connected between said bulb and said intubation tube such that in response to expansion of said bulb, negative pressure is generated in said connection device and in said intubation tube.

13. The connection device of claim 10, wherein the rate of expansion and contraction of said bulb indicates the location of an intubation tube placed in a patient.

14. The connection device of claim 1, wherein said volume displacement detector is a syringe.

15. The connection device of claim 14, wherein said syringe comprises first and second barrels with first and second orifices and a plunger configured to fit into said first or second barrels, said syringe being detachably connected to said connection device at said second orifice with an adapter.

16. The connection device of claim 15, wherein withdrawal of said plunger from said syringe provides an physical indication of whether an intubation tube is properly placed.

17. The connection device of claim 16, wherein said physical indication comprises resistance to movement of said plunger or free movement of said plunger.

18. The connection device of claim 17, wherein said resistance to movement of said plunger is indicative of esophagael intubation, and free movement of said plunger is indicative of tracheal intubation.

19. The connection device of claim 18, wherein said gas composition detector is connected to said connection device such that upon application of positive pressure in said system, said positive pressure response valve opens allowing gas obtained from said patient to communicate with said gas composition detector device.

20. The connection device of claim 19 wherein said positive pressure is created through movement of said plunger barrel toward said second orifice of said syringe.

21. The connection device of claim 10, wherein said positive pressure in said first and second conduits is created through compression of said bulb.

22. The connection device of claim 1, wherein said gas composition detector utilizes a colorimetric indicator to indicate the presence of a specified gas.

23. The connection device of claim 22, wherein said gas is carbon dioxide.

24. The connection device of claim 23, wherein a change in color of said indicator when exposed to said gas is indicative of tracheal intubation.

25. The connection device of claim 24, wherein said gas composition detector does not require calibration.

26. The connection device of claim 25, wherein said gas composition detector is operable without a power source.

27. The connection device of claim 26, wherein said gas composition detector is a capnometer.

* * * * *